US009936186B2

(12) United States Patent
Jesenko et al.

(10) Patent No.: US 9,936,186 B2
(45) Date of Patent: Apr. 3, 2018

(54) METHOD FOR CONTINUATION OF IMAGE CAPTURE FOR ACQUIRING THREE-DIMENSIONAL GEOMETRIES OF OBJECTS

(71) Applicant: a.tron3d GmbH, Klagenfurt am Wörthersee (AT)

(72) Inventors: Jurgen Jesenko, Finkenstein (AT); Horst Koinig, Klagenfurt (AT)

(73) Assignee: A.TRON3D GMBH, Klagenfurt am Worthersee (AT)

( * ) Notice: Subject to any disclaimer, the term of this patent is extended or adjusted under 35 U.S.C. 154(b) by 405 days.

(21) Appl. No.: 14/377,587

(22) PCT Filed: Jun. 3, 2013

(86) PCT No.: PCT/AT2013/000094
§ 371 (c)(1),
(2) Date: Aug. 8, 2014

(87) PCT Pub. No.: WO2013/181678
PCT Pub. Date: Dec. 12, 2013

(65) Prior Publication Data
US 2015/0009293 A1    Jan. 8, 2015

(30) Foreign Application Priority Data
Jun. 5, 2012    (EP) .................................... 12170858

(51) Int. Cl.
*G06T 19/20* (2011.01)
*H04N 13/02* (2006.01)
*A61C 9/00* (2006.01)

(52) U.S. Cl.
CPC ......... *H04N 13/0207* (2013.01); *A61C 9/004* (2013.01); *G06T 19/20* (2013.01);
(Continued)

(58) Field of Classification Search
None
See application file for complete search history.

(56) References Cited

U.S. PATENT DOCUMENTS 7,065,091 B2    6/2006    Shoham et al.
7,212,535 B2    5/2007    Shoham et al.
(Continued)

FOREIGN PATENT DOCUMENTS

AT    508 563    5/2011
EP    1 424 656    6/2004

OTHER PUBLICATIONS

International Search Report dated Sep. 6, 2013, corresponding to PCT/AT2013/000094.
(Continued)

*Primary Examiner* — Jayanti K Patel
*Assistant Examiner* — Shadan E Haghani
(74) *Attorney, Agent, or Firm* — Young & Thompson

(57) ABSTRACT

A method for capturing at least one sub-region of a three-dimensional geometry of at least one object, for the purpose of updating an existing virtual three-dimensional geometry of the sub-region, optionally after elements of the object present in the sub-region have been modified, removed and/or added, wherein the method includes the following steps: a) providing the existing virtual three-dimensional geometry of the object, for example, from an earlier image capture, b) capturing of two-dimensional images from which spatial information of the three-dimensional geometry of the objects is obtained, c) automatic addition of spatial information obtained to existing spatial information, if applicable d) updating the existing virtual three-dimensional geometry of the sub-region of the object based on added information, e) optionally repeating the process from step b).

18 Claims, 3 Drawing Sheets

(52) U.S. Cl.
CPC ............... *G06T 2219/2021* (2013.01); *H04N 2213/003* (2013.01)

(56) References Cited

U.S. PATENT DOCUMENTS

| | | | |
|---|---|---|---|
| 7,403,648 B2 | 7/2008 | Nakamura | |
| 9,613,420 B2* | 4/2017 | Tamaazousti | G06T 7/579 |
| 2003/0214964 A1 | 11/2003 | Shoham et al. | |
| 2004/1017018 | 6/2004 | Nakamura | |
| 2005/0057561 A1* | 3/2005 | El-Din ElShishiny | G06T 17/20 |
| | | | 345/419 |
| 2006/0176883 A1 | 8/2006 | Shoham et al. | |
| 2007/0103460 A1* | 5/2007 | Zhang | G06T 7/285 |
| | | | 345/419 |
| 2007/0172101 A1* | 7/2007 | Kriveshko | A61B 5/4547 |
| | | | 382/128 |
| 2008/0012850 A1* | 1/2008 | Keating, III | H04N 13/0207 |
| | | | 345/419 |
| 2009/0073257 A1* | 3/2009 | Tanaka | G06T 17/00 |
| | | | 348/45 |
| 2009/0128546 A1* | 5/2009 | Masuda | G06T 7/35 |
| | | | 345/419 |
| 2010/0060885 A1* | 3/2010 | Nobis | G01B 11/2755 |
| | | | 356/139.09 |
| 2011/0298891 A1* | 12/2011 | Zhang | G01B 11/2509 |
| | | | 348/43 |
| 2012/0194517 A1* | 8/2012 | Izadi | G06T 17/00 |
| | | | 345/420 |
| 2012/0306876 A1* | 12/2012 | Shotton | G06T 17/10 |
| | | | 345/424 |
| 2015/0161476 A1* | 6/2015 | Kurz | G06K 9/4671 |
| | | | 382/190 |

OTHER PUBLICATIONS

Richard A. Newcombe, et al.; "KinectFusion: Real-Time Dense Surface Mapping and Tracking"; Oct. 26, 2011; pp. 127-136.

* cited by examiner

METHOD FOR CONTINUATION OF IMAGE CAPTURE FOR ACQUIRING THREE-DIMENSIONAL GEOMETRIES OF OBJECTS

BACKGROUND OF THE INVENTION

Field of the Invention

The invention relates to a method for capturing at least a sub-region of a three-dimensional geometry of at least one object, in particular a tooth and/or an organic and/or inorganic structure that is brought into the oral space, for example a dental implant, for the purpose of updating an already existing, virtual three-dimensional geometry of the sub-region, optionally after elements of the object located in the sub-region have been modified, removed and/or added.

Description of the Related Art

Methods for optical acquisition of three-dimensional geometries are known from the state of the art, for example from AT 508 563 A. A problem arises, however, when a three-dimensional virtual geometry, for example originating from an earlier capture, is to be supplemented or changed, for example after modifications of the object, which can occur, e.g., within the framework of a dental treatment.

To date, this problem has just been avoided by running a completely new capture, whose data initially stand for themselves. Only in later process steps is this new image capture then placed over the existing one or "sewn" to the latter. This process causes inaccuracies and can in part be performed or calculated only offline, i.e., not during the image capture itself.

BRIEF SUMMARY OF THE INVENTION

The purpose of the invention is therefore to make available a method that overcomes the above-mentioned drawbacks.

This object is achieved by a method with the features disclosed below.

In one embodiment, first the already existing, virtual three-dimensional geometry is made available. Availability is made in this case independently of a display, in the form of previously existing data from the surface geometry of the object, for example in the form of n-tuples. The already existing, virtual three-dimensional geometry thus is not separate as in the known avoidance approaches but is rather the basis of the new virtual three-dimensional geometry that is to be acquired or updated. Methods in which the virtual three-dimensional geometry is not made available in n-tuples but rather other volumetric or non-volumetric data are also conceivable.

Providing can represent both the calling-up of a file and the accessing of already loaded data, for example after an intended or accidental short interruption of an image capture.

After the virtual three-dimensional geometry has been made available, at least two two-dimensional images are captured, from which spatial information on the three-dimensional geometry is derived. This can take place by, for example, as proposed according to a preferred embodiment, the images being captured as sets of images, whereby a set of images in each case consists of at least two predominantly overlapping images of the same capturing area. Thus, for example, disparities can be determined that supply the spatial information. Other methods known from the state of the art, in which spatial information from two-dimensional images can be obtained, are also conceivable, whereby the way in which the spatial information is obtained is not important for the method according to the invention.

As an alternative, therefore, an image can also be captured while at the same time, a known pattern is projected. If a projected pattern is known, spatial information can be obtained from the distortion, which is produced in the projection on a non-flat surface.

The spatial information, which was obtained by the two alternative process steps according to the invention, is then automatically introduced into the already existing, virtual three-dimensional geometry. This can be carried out with a simple plausibility query, in which the newly obtained spatial information, in particular characteristics, such as, for example, the curvature of the surface or distances from spatial points, are compared to those of the existing, virtual three-dimensional geometry.

This process can be accelerated, according to a preferred embodiment of the invention, by a manual selection of the sub-region to be updated being carried out in a visualization of the existing, virtual three-dimensional geometry, since the amount of n-tuples to be compared, in particular volume points or voxel, is reduced.

After the addition, the virtual three-dimensional geometry is updated. Thus, unlike before, no completely new, separate geometry with subsequent approximation is compiled, but rather additional information is added to the existing information. Since it can be proven mathematically, that more information to a voxel also increases the accuracy of the voxel, no uncertainties are produced by the adding of the information, contrary to stitching or superimposing, but the accuracy of the virtual three-dimensional model is increased.

If the entire sub-region to be updated has still not been acquired or updated by the first capture, the method can be repeated starting from the image capture until the entire sub-region to be updated has been acquired or updated.

According to a preferred embodiment of the invention, the provided, existing, virtual three-dimensional geometry can be visualized by means of a medium, for example a screen, which is easy for the user to read. The data are thus converted into a representation of the data, for example, by means of the known ray-casting method. In this case, aside from the already mentioned screen, for example, a hologram can also be a medium that is easy to read.

In a preferred embodiment of the invention, visualization can also be carried out on a 3D screen. Thus, the user, with the aid of corresponding 3D glasses, has an actual three-dimensional perception of the visualized data.

Analogously to this, according to another preferred embodiment of the invention, the updated virtual three-dimensional geometry can be visualized in connection to the updating of the virtual three-dimensional geometry.

According to a quite especially preferred embodiment of the invention, in this case both the addition and the visualization are carried out essentially in real time. Between the beginning of the capture for updating and the visualization of the updated virtual three-dimensional geometry, there is thus a period that is imperceptible for the user. The processes are perceived essentially simultaneously.

In another preferred embodiment of the invention, the visualisation contains information regarding accuracy of the acquired virtual three-dimensional geometry. Since the accuracy of the virtual three-dimensional geometry or the individual voxel increases by the number of available pieces of information, for example, areas can be colored according to the amount of information. An example of this that is simple and can be grasped intuitively would be a color gradient of red-yellow-green, whereby with an increasing number of pieces of information per volume point, the latter slowly changes color from red to green.

In addition or as an alternative, optical references to advisable improvements of the image capture for an operator can be added to the display, for example direction indicators. Thus, the user, for example, can be called upon to make additional image captures with an arrow from a specific area in order to achieve higher accuracy.

According to a preferred embodiment of the invention, the sets of images are captured stereometrically. A set of images is in this case captured simultaneously from at least two cameras that are arranged offset to one another and that are oriented to an essentially identical image capture area.

As a result, primarily time can be saved. On the one hand, no time thus elapses between the image captures of the individual images since the latter are made simultaneously. On the other hand, in the case of stereometric image captures for the determination of spatial information, important benchmarks, such as the orientation and position of the camera, are known and constant and therefore neither need be determined nor co-calculated as variable in the case of a calculation.

According to another preferred embodiment of the invention, acoustic signals for accuracy of the acquired virtual three-dimensional geometry can be provided based on the image capture area of a device for capturing images, in particular sets of images. Thus, for example, while an area is being captured about which already a lot of information is available, a high-pitched tone can sound, and while an area is being captured about which still insufficient captures are available for a desired accuracy, a deeper tone can sound.

According to a preferred embodiment of the invention, at least during the capture, a pattern is projected on the sub-region. This can be a random pattern, which consists of randomly distributed, optionally irregularly formed points and/or lines, or a regular pattern, for example a striped pattern. The projection of patterns simplifies the determination of spatial information. In this case, the projection should be carried out during the capture, but it can also be projected as early as before and/or even after the capture.

In this case, a random pattern is defined as a pattern that has as few repetitions as possible, i.e., is explicitly non-ordered. In this case, with each image capture, the same random pattern can be projected. A random pattern can be known or unknown.

According to another preferred embodiment of the invention, the updated virtual three-dimensional geometry is converted into an Open Source Format, for example STL. As a result, the data can be relayed to third parties, for example a dental laboratory. This can be done directly, for example via an Internet connection, or indirectly, by means of a data medium, for example a CD or a USB stick.

Embodiments in which the determined virtual three-dimensional geometry is directly used without further conversion to another format, for example by a machine for milling prosthetic dental elements, are also conceivable. Thus, for example, after the exact forms of a dental preparation have been captured, a matching crown can be fabricated.

According to an additional embodiment of the invention, possible flaws in the virtual three-dimensional geometry are determined, and in the course of the conversion, a virtual three-dimensional geometry of the flaws without image capture of other spatial information is determined based on the areas surrounding the flaws. To this end, certain characteristics of the surrounding areas, such as their curvature or distances from the image plane, are used. By means of the latter, the virtual three-dimensional geometry of the flaws is then preferably interpolated and/or extrapolated.

Other preferred embodiments and implementations of the invention are subject of the other subclaims.

BRIEF DESCRIPTION OF THE DRAWINGS

The invention is further explained below with reference to the drawings. Here.

DETAILED DESCRIPTION OF THE PREFERRED EMBODIMENTS

Figure 1:
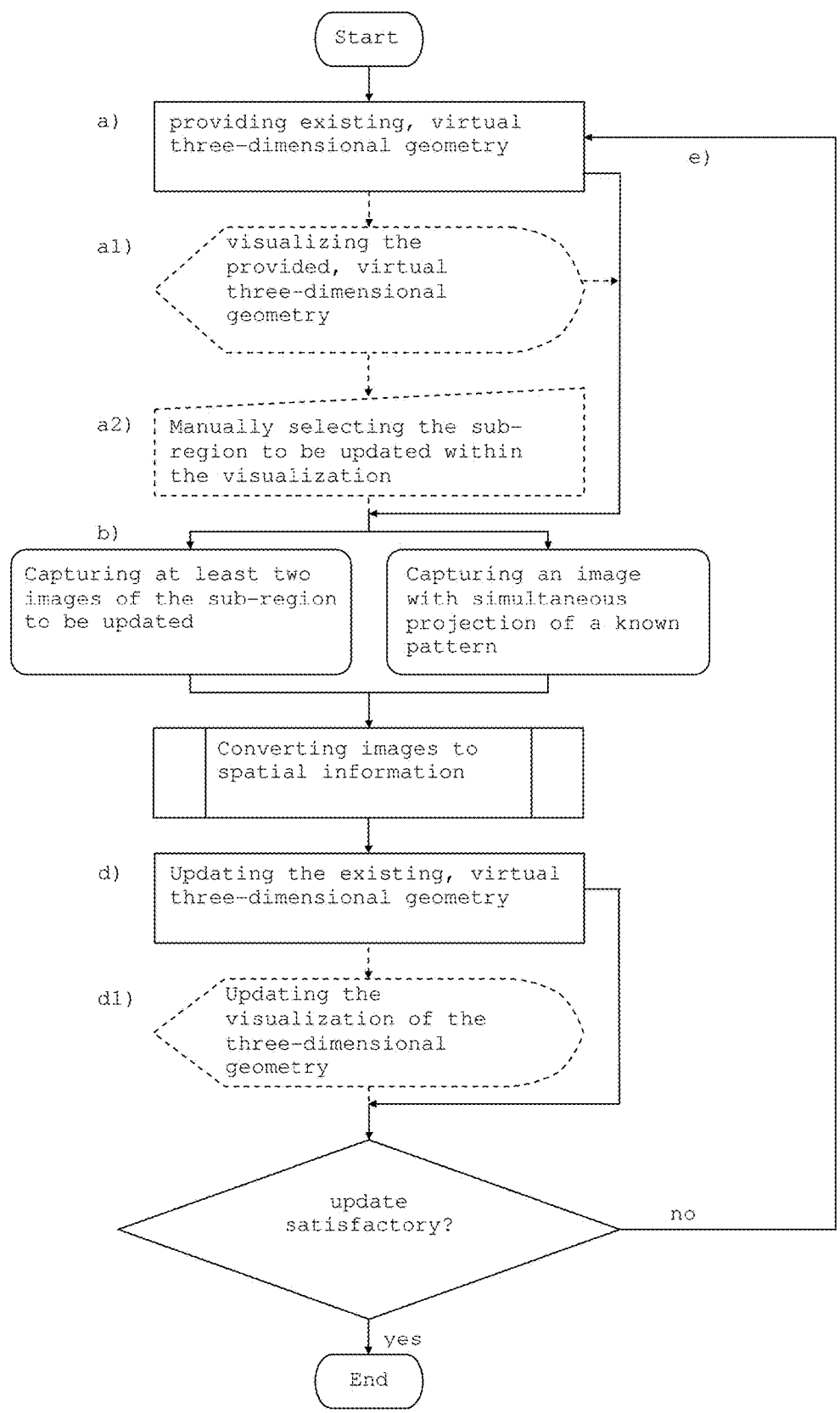
FIG. 1 shows an exemplary embodiment of the method according to the invention.

FIG. 1 shows an embodiment, according to the invention, of the sequence of the method. In this case, first an existing, virtual three-dimensional geometry is provided originating from, for example, an earlier capture. The latter can optionally already be visualized. When the latter is displayed, a sub-region that is to be updated can also optionally be selected in the visualization. Thus, the method can be accelerated. For the functionality of the method, this step, however, is not imperative.

Then, the sub-region that is to be updated is captured. This can be done according to a first embodiment of the method by an image being captured with simultaneous projection of a known pattern. The type of pattern, i.e., whether in this case, for example, it is a regular striped pattern or a random pattern, is not decisive here for the invention since in any case, because of the surface structure of the sub-region to be captured, it results in distortions of the known pattern, from which spatial information on the sub-region to be updated can be obtained.

As an alternative, at least two images can preferably be captured simultaneously from which spatial information can also be obtained.

The spatial information that is obtained is then used for updating the virtual three-dimensional geometry. Optionally, the latter can then also be visualized.

If the updating is satisfactory, the method is completed. Criteria in this respect, whether the updating is satisfactory, can in this case, for example, be the achieving of a desired accuracy or the complete acquisition of the sub-region to be updated. The latter criterion cannot be met, for example, when an image capture area of a device for capturing the images or the image is smaller than the sub-region that is to be updated.

When the updating is unsatisfactory, the process is repeated. The updated, virtual three-dimensional geometry, as described above, is in this case now the existing, available, virtual three-dimensional geometry.

Figure 2:
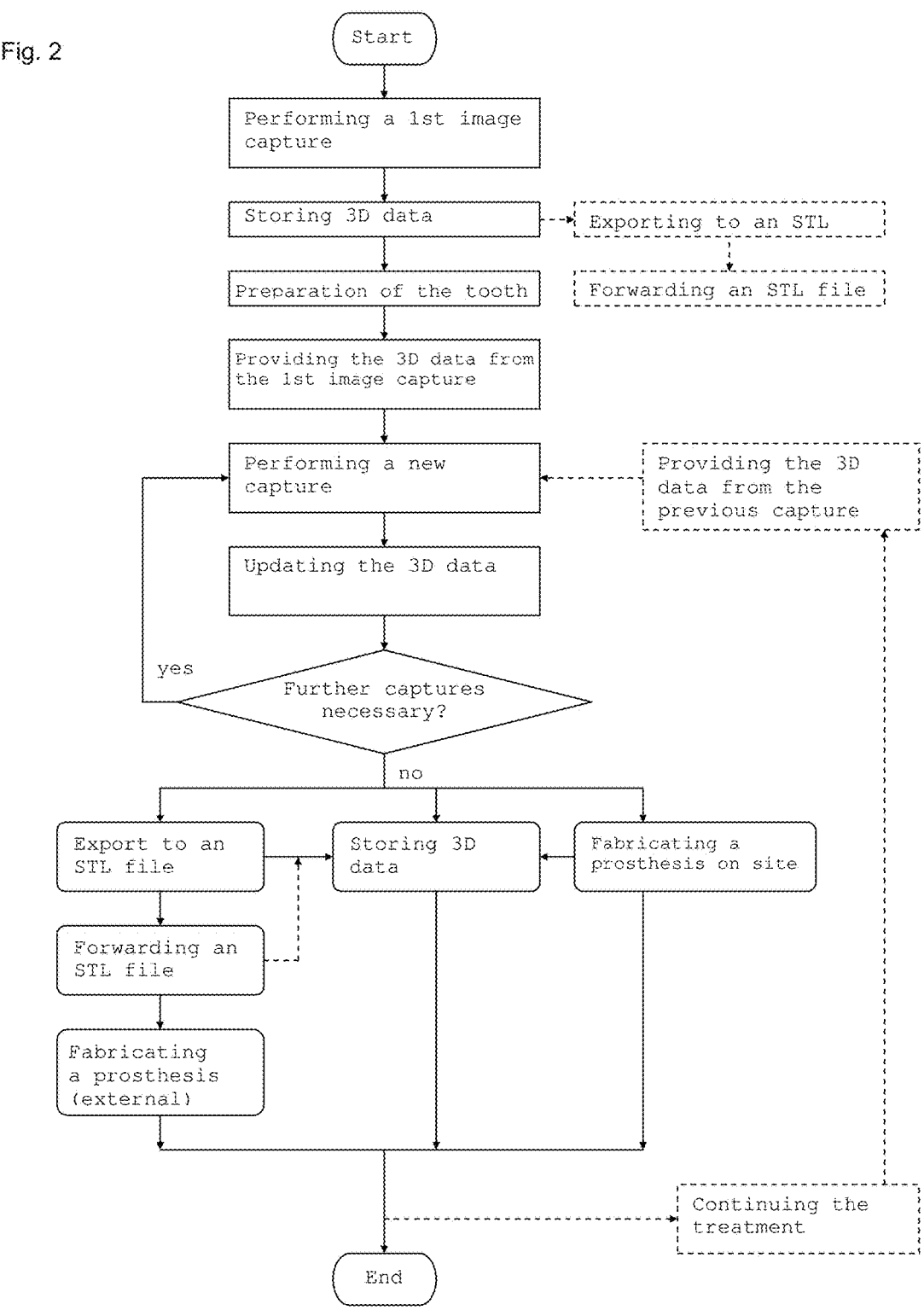
FIG. 2 shows an exemplary application of the method according to the invention.

FIG. 2 shows an exemplary application of the method according to the invention.

In this case, for example, in the case of a patient who resorts to a dental treatment, a first image capture is initially performed. With the latter, for example, spatial information of the teeth of the upper and lower jaw of the patient can be acquired and converted into a virtual three-dimensional geometry ("3D data" below). Of course, even from the outset, only a sub-region of the oral space can be captured. Likewise, in addition to the teeth, possibly already existing crowns, braces, implants, veneers or the like can also be captured as part of the 3D data.

The 3D data from the first capture are then stored; in addition, they can optionally be exported to an STL file in order to then optionally be forwarded. The STL format is in this case preferred, since it involves an Open Source Format that in general can be opened by all dental laboratories. The 3D data on the starting situation of the patient are available to these laboratories by the forwarding.

Subsequently, the patient receives a dental treatment. In this case, as depicted in the embodiment, this can be the preparation of a tooth, for example, for a crown. Other types of treatment are also conceivable, of course.

At a later time, for example directly after the preparation, the 3D data of the first image capture are provided. The period that has taken place since the first image capture in this case plays no role for the application of the method according to the invention. Thus, for example, even a period of several weeks since the first image capture may have elapsed, as may be the case, for example, with follow-up appointments for orthodontic measures.

After providing the 3D data, a new capture is made. Thereby the entire originally captured area can be captured again as well as only a sub-region that should be updated after a change or as a checkup. In this case, changes comprise not only the results of dental treatments. For example, the natural growth of a wisdom tooth and its impacts on the other teeth can also be a change that should be updated in the 3D data.

If other captures are necessary, for example in order to increase the accuracy, the last two steps of the method are repeated. If no other image captures are necessary, several alternative possibilities are available to the user, which can be performed separately or as a supplement to one another.

On the one hand, the 3D data can be easily stored for further use. On the other hand, if the necessary technical systems are available, a prosthesis can be fabricated on the spot in the dental practice.

An export to an STL file represents a third possibility. The latter can then be forwarded again in order to allow a prosthesis to be fabricated in a dental laboratory.

When the treatment is to be pursued, the updated 3D data are again provided at a later time, and the process can be repeated starting from the capture of the images or of the image. Otherwise, the process ends.

Figure 3:
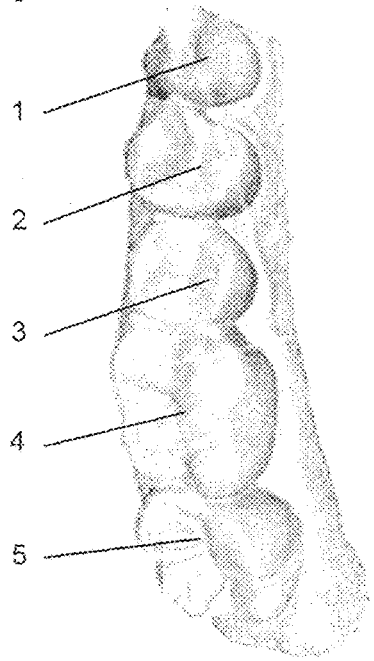
FIG. 3 shows a visualized, provided, virtual three-dimensional geometry from a first point of view.

FIG. 3 shows a visualized, provided, virtual three-dimensional geometry of a jaw arch section from a first point of view. In the visualisation, five teeth 1, 2, 3, 4, 5 can be seen. The provided geometry in this case originates from an earlier capture. The displayed elements are in this case teeth as well as the oral space with the gum surrounding them. However, additional elements of the sub-region could already also be located in the provided capture, such as, for example, crowns, braces or the like. In this case, an element of the sub-region in principle comprises all elements that can be visually acquired and captured in the sub-region.

Figure 4:
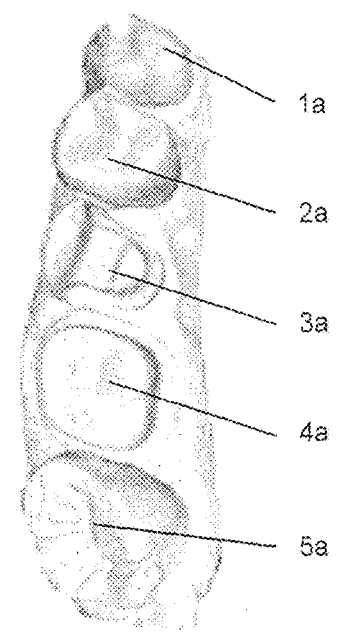
FIG. 4 shows the visualized, updated, virtual three-dimensional geometry of FIG. 3 after a preparation.

FIG. 4 shows a visualized, updated, virtual three-dimensional geometry of the same sub-region as in FIG. 3 from the same point of view as in FIG. 3. It is recognized that elements of the sub-region were changed. In the depicted example, the original teeth 3, 4 were prepared for the installation of dental prostheses. It can be clearly seen on the teeth 3a, 4a that substance was worn away. The teeth 1a, 2a and 5a are unchanged.

In this case, the depicted change is only one example of a type of change. Of course, changes can also be captured, such as the addition of substance, for example the application of a crown, or simple positional changes of elements of the sub-region, for example after an orthodontic correction of dental defects.

Figure 5:
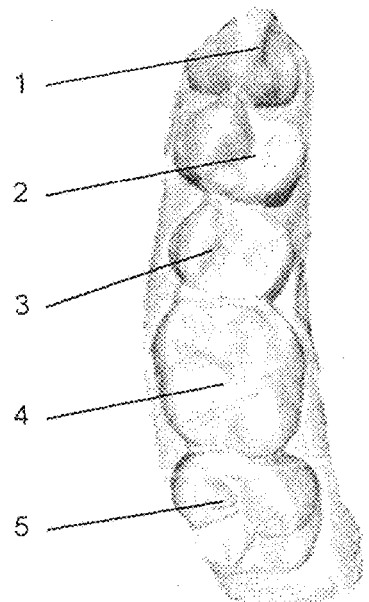
FIG. 5 shows the visualized, provided, virtual three-dimensional geometry of FIG. 3 from a second point of view.

FIG. 5 shows the displayed, available, virtual three-dimensional geometry of FIG. 3 from a second point of view. In this case the change of point of view can be made based upon simple user input and is independent of the direction from which the images of the sub-region are made or have been made earlier. In this case, the input can optionally be carried out, for example, via simple operating elements depicted in a display. The latter can be used, for example, via a computer mouse or else via a touchscreen.

A simple modification by computer of the point of view in ray-casting in order to change a point of view is known from the state of the art.

Figure 6:
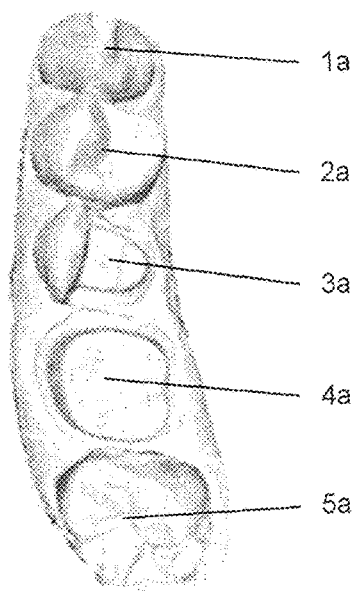
FIG. 6 shows the visualized, updated, virtual three-dimensional geometry of FIG. 3 from the second point of view.

FIG. 6 shows the visualized, updated, virtual three-dimensional geometry of FIG. 4 from the point of view of FIG. 5. The changes in the course of updating can again be recognized.

The invention claimed is:

1. A method for image capture of at least one sub-region of a three-dimensional geometry of at least one object contained within an already existing three-dimensional geometry of the at least one object, in particular of a tooth and/or of an organic and/or inorganic structure that is brought into the oral space, including of a dental implant, for the purpose of updating the sub-region in the already existing, virtual three-dimensional geometry of the object, optionally after elements of the object located in the sub-region have been modified, removed and/or added, whereby the method includes the following steps:

a) Making available the already existing, virtual three-dimensional geometry of the object, b) Capturing at least two two-dimensional images of a sub-region that is entirely within the already existing, virtual three-dimensional geometry of the object, from which at least two two-dimensional images additional spatial information of the three-dimensional geometry of the object is obtained, c) Automatically adding the additional spatial information of the three-dimensional geometry of the object that is obtained in said capturing step b) to already existing spatial information of the already existing, virtual three-dimensional geometry of the object, d) Updating the already existing, virtual three-dimensional geometry of the sub-region of the object based on the added additional spatial information to obtain an updated virtual three-dimensional geometry of the sub-region of the object, e) Optionally repeating the process starting from Step b), wherein, in said step d), the updating of the already existing, virtual three-dimensional geometry of the sub-region of the object based on the added additional spatial information, to obtain an updated virtual three-dimensional geometry of the sub-region of the object, includes at least one of the group consisting of:
  i) comparing a curvature of a surface from the additional spatial information of the three-dimensional geometry of the sub-region to a curvature of the surface from the already existing spatial information of the already existing, virtual three-dimensional geometry of the sub-region, and
  ii) comparing distances from spatial points from the additional spatial information of the three-dimensional geometry of the sub-region to distances of the spatial points from the already existing spatial information of the already existing, virtual three-dimensional geometry of the sub-region.

2. The method according to claim 1, further comprising, after Step a), the step of:
  a1) Displaying the already existing, virtual geometry by means of a medium that is readable by a user.

3. The method according to claim 2, further comprising, after Step a1), the step of:
  a2) Manually selecting the sub-region to be updated from the displayed virtual geometry.

4. The method according to claim 2, wherein the display contains information regarding accuracy of the acquired virtual three-dimensional geometry.

5. The method according to claim 2, wherein optical references to advisable improvements of the image capture for an operator are added to the display.

6. The method according to claim 2, wherein the display is carried out on a 3D screen.

7. The method according to claim 1, further comprising, after Step d), the step of:
  d1) Updating the displayed already existing, virtual three-dimensional geometry based on the obtained updated virtual three-dimensional geometry of the sub-region of the object.

8. The method according to claim 7, wherein a time period between a beginning of the capture of the at least two two-dimensional images in step b) and the updating the displayed already existing, virtual three-dimensional geometry based on the obtained updated virtual three-dimensional geometry of the sub-region of the object in step d1) is imperceptible for the user.

9. The method according to claim 1, wherein the at least two two-dimensional images are captured as sets of images, whereby one set of images in each case consists of at least two predominantly overlapping image captures of an identical image capture area.

10. The method according to claim 9, wherein the sets of images are captured stereometrically.

11. The method according to claim 1, wherein acoustic signals for accuracy of the acquired virtual three-dimensional geometry are provided based on the image capture area of a device for capturing images, in particular sets of images.

12. The method according to claim 1, wherein a pattern is projected on the sub-region at least during the capture of the at least two two-dimensional images.

13. The method according to claim 1, wherein a random pattern is projected, whereby the random pattern consists of randomly distributed, optionally irregularly formed points and/or lines.

14. The method according to claim 1, wherein a regular pattern, is projected.

15. The method according to claim 1, wherein the updated virtual three-dimensional geometry is converted into an Open Source Format.

16. The method according to claim 15, wherein possible flaws in the virtual three-dimensional geometry are determined, and wherein in the course of the conversion, a virtual three-dimensional geometry of the flaws without image capture of other spatial information is determined based on the areas surrounding the flaws.

17. The method according to claim 16, wherein the virtual three-dimensional geometry of the flaws is determined by means of interpolation and/or extrapolation.

18. The method according to claim 1, further comprising, after Step a), the step of:
  a1) Displaying the already existing, virtual geometry by means of a medium that is readable by a user.

* * * * *